(12) United States Patent
Drevik

(10) Patent No.: US 6,586,654 B2
(45) Date of Patent: Jul. 1, 2003

(54) SANITARY NAPKIN

(75) Inventor: Solgun Drevik, Molnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/832,843

(22) Filed: Apr. 12, 2001

(65) Prior Publication Data

US 2001/0053900 A1 Dec. 20, 2001

Related U.S. Application Data

(60) Provisional application No. 60/200,355, filed on Apr. 28, 2000.

(30) Foreign Application Priority Data

Apr. 13, 2000 (SE) .............................................. 0001377

(51) Int. Cl.$^7$ ................................................ A61F 13/15
(52) U.S. Cl. ................................... 604/378; 604/385.04
(58) Field of Search ........................ 604/385.01, 385.03, 604/385.04, 385.06, 385.05, 386, 387, 378

(56) References Cited

U.S. PATENT DOCUMENTS

| | | | |
|---|---|---|---|
| 5,454,804 A | | 10/1995 | Widlund |
| 5,683,373 A | | 11/1997 | Darby |
| 5,713,886 A | * | 2/1998 | Sturino ................. 604/385.04 |
| 5,729,835 A | * | 3/1998 | Williams ........................ 2/400 |
| 5,797,894 A | | 8/1998 | Cadieux et al. |
| 5,895,379 A | * | 4/1999 | Litchholt et al. ........... 604/368 |

FOREIGN PATENT DOCUMENTS

| | | |
|---|---|---|
| DE | 295 13548 | 2/1996 |
| WO | WO 94/09737 | 5/1994 |
| WO | WO 94/10956 | 5/1994 |
| WO | WO 00/30585 | 6/2000 |

* cited by examiner

Primary Examiner—Weilun Lo
Assistant Examiner—Jamisue A. Webb
(74) Attorney, Agent, or Firm—Young & Thompson

(57) ABSTRACT

An absorbent article aritcle for women includes an absorbent body which is sandwiched between a liquid-permeable outer sheet and a liquid-impermeable outer sheet. The article has a front part, which is intended to face forwards when the article is worn, and a rear part. The absorbent body has a length of 140–260 mm and tapers rearwardly from a section of greatest width situated in the front part of the article to the end of the rear part of the article. The absorbent body has a widest width of 60–80 mm in its front part, and a smallest width of 5–20 mm in its rear end, and includes a layer of dry-formed cellulose fibers having a density of at least 250 g/dm$^3$ and extending over essentially the whole surface of the absorbent body, out to the front and side edges of the body. of a sanitary napkin, a panty liner or an incontinence protector for women comprising an absorbent body (2) which is sandwiched between a liquid-permeable outer sheet (3) and a liquid-impermeable outer sheet (4), said article having a front part (5), which is intended to face forwards when the article is worn, and a rear part, wherein the absorbent body has a length of 140–260 mm and tapers rearwardly from a section of greatest width situated in the front part of the article to the end of the rear part of said article. According to the invention, the absorbent body (2) has a widest width of 60–80 mm in its front part, and a smallest width of 5–20 mm in its rear end, and includes a layer (13) of dry-formed cellulose fibres having a density of at least 250 g/dm$^3$ and extending over essentially the whole surface of the absorbent body, out to the front and side edges of said body.

12 Claims, 1 Drawing Sheet

SANITARY NAPKIN

This application claims the benefit of Provisional application Ser. No. 60/200,355 filed Apr. 28, 2000.

FIELD OF INVENTION

The present invention relates to an absorbent article in the form of a sanitary napkin, a panty liner or an incontinence protector for women, comprising an absorbent body which is sandwiched between a liquid-permeable and a liquid-impermeable outer sheet, and having a front part which is intended to face forwards where the article is worn, and a rear part, wherein the absorbent body has a length of 140–260 mm and tapers rearwardly from a section of greatest width situated in the front part of the napkin down to the end of said rear part.

BACKGROUND OF THE INVENTION

A sanitary napkin of this kind is intended to be worn in so-called string panties, the rear portion of the crotch part of which is extremely narrow. String panties are primarily worn for aesthetic reasons and are practically invisible even when worn beneath tightly fitting garments. Naturally, high demands are placed on sanitary napkins that shall be worn together with string panties, which napkins must have a very narrow rear portion and also be very thin so that they can be worn discretely. Such napkins shall also fulfil requirements relating to effective absorption properties and shall also be comfortable to wear.

The object of the present invention is to provide an absorbent article of the aforedescribed kind that fulfils discretion requirements without detracting from the absorption properties and comfort of the article.

SUMMARY OF THE INVENTION

This object is achieved with an absorbent article in the form of a sanitary napkin, a panty liner or an incontinence protector for women that includes an absorbent body enclosed between a liquid-permeable outer sheet and a liquid-impermeable outer sheet, said article having a front part which is intended to face forwards when the article is worn, and a rear part, wherein the absorbent body has a length of 140–260 mm and tapers rearwardly from a section of greatest width situated in the front part of the napkin to the end of the rear part thereof, and wherein the article is characterised in that the absorbent body has a greatest width of 60–80 mm in its front part, and a smallest width of 5–20 mm in its rear part, and includes a layer of dry-formed cellulose fibre having a density of at least 250 g/m$^3$ and extending over substantially the whole of the absorbent body, right out to its front and side edges. Because the layer of dry-formed fibres extends over substantially the entire absorbent body, the absorbent properties of said material can be fully utilised, and because the layer has been given a high density, and therewith has fine capillaries, the layer is able to effectively disperse discharged liquid in the layer. This enables the absorbent body to be made thin. Furthermore, the dimensions of the article together with the physical properties of the absorbent layer enable the article to be worn comfortably.

In one preferred embodiment of the invention, the layer of dry-formed cellulose fibres has a weight per unit area of 200–600 g/m$^2$ and the absorbent body also includes a layer of material that has good liquid acquisition properties and that extends over the whole of the layer of dry-formed cellulose fibres and beyond said layer to the rear end-part of the absorbent body. The material having good liquid acquisition properties may be comprised of a fibre wadding of cellulose fibres, synthetic fibres or mixtures thereof. The article will also preferably include outwardly projecting, flexible flaps which extend outwardly of the absorbent body on respective sides thereof, along a part of the tapering portion of said body. The flaps may form integral parts of at least one of the outer sheets. The article also includes at least one fastener means on that part of the napkin which includes the absorbent body and on at least one flap, for fastening the article to a panty. The fastener means may conveniently comprise strings of pressure-sensitive glue, e.g. hotmelt glue.

BRIEF DESCRIPTION OF THE DRAWINGS

The present invention will now be described with reference to the accompanying drawings, in which.

DESCRIPTION OF EMBODIMENTS

Figure 1:
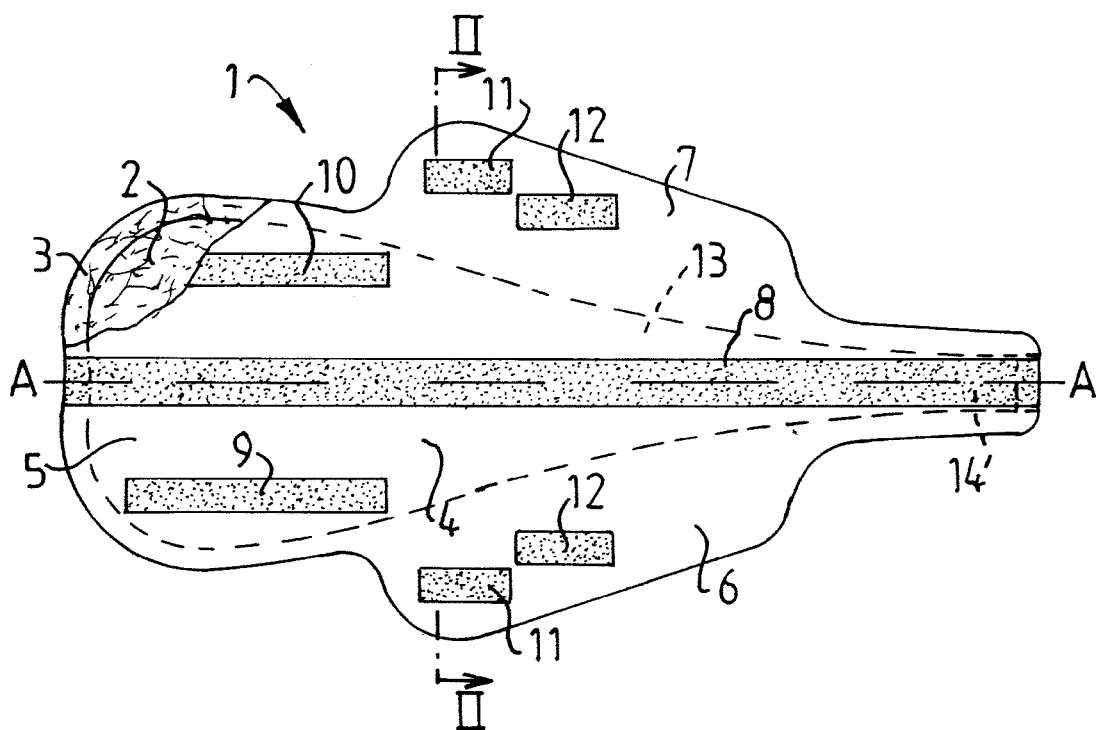
FIG. 1 illustrates schematically in partially cut-away plan view a first embodiment of an inventive sanitary napkin, with the liquid-impermeable outer sheet facing towards the viewer.
Figure 2:
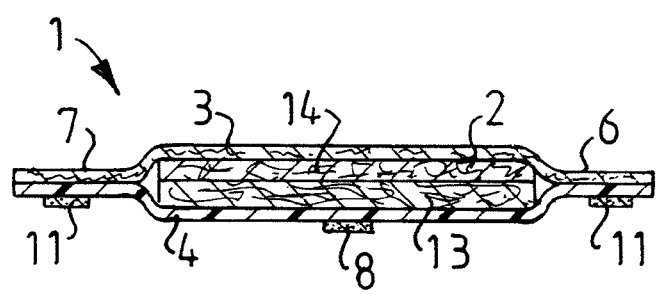
FIG. 2 is a sectional view taken on the line II—II in FIG. 1, with the liquid-permeable outer sheet facing upwards.

The sanitary napkin 1 illustrated in the drawing typically includes an absorbent body 2 enclosed between a liquid-permeable outer sheet 3 and a liquid-impermeable outer sheet 4. The outer sheets 3, 4 are joined together at parts located outwardly of the absorbent body in some suitable way, e.g. by gluing or by ultrasound welding or heat welding.

The sanitary napkin 1 is intended for wear in a string panty and the absorbent body 2 accordingly tapers rearwardly from the widest part of the front portion 5 of the napkin to its rear end. The outer sheets 3, 4 form outwardly projecting flaps 6, 7, or wings, which are intended to be folded around the edges of a string panty and fastened to the outside thereof. The flaps 6, 7 extend longitudinally outwardly of the edges of the absorbent body with essentially the same widths, and the longitudinal edges of the flaps therewith converge towards each other in the rearward direction. In the case of the illustrated embodiment, the length of the flaps corresponds to about half the length of the napkin and the flaps are placed at a slightly greater distance from the front end of the napkin than from its rear end.

The napkin has a length of 140–260 mm. The absorbent body has a greatest width of 60–80 mm, preferably about 70 mm, and a smallest width at its rear end of 5–20 mm, preferably about 10 mm. The flaps extend beyond the edges of the absorbent body through a distance of about 25–30 mm, with the greatest distance in the front parts of the flaps. The front edges of the flaps are located about 60 mm from the front edge of the napkin, and the rear edges of the flaps are located about 50 mm from the rear end of said napkin. It will be understood that the aforesaid flap measurements have merely been given to provide a qualitative understanding of a suitable flap design on a sanitary napkin intended for string panties and in no way limit the scope of the invention.

The liquid-permeable outer sheet 3 is comprised of a soft, skin-friendly material. This outer sheet may comprise a sheet of different types of nonwoven fibre material. Other materials that can be used are perforated plastic film, plastic net, knitted, crocheted or woven textiles, and combinations and laminations of the aforesaid types of material. The plastic may be a thermoplastic, e.g. polyethylene (PE). The nonwoven material may comprise natural fibres, such as cellulose or cotton, although it may alternatively comprise synthetic fibres, such as polyethylene (PE), polypropylene (PP), polyurethane (PU), a polyester, nylon or regenerated cellulose, or a mixture of different fibres. All materials that are used to produce liquid-permeable outer sheets for absorbent articles, such as sanitary napkins, panty liners or incontinence protectors, can be used for the liquid-permeable outer sheet 3, and it will be understood that the aforesaid materials have merely been given by way of example.

The liquid-impermeable outer sheet 4 may comprise a flexible material, preferably a thin plastic film of polyethylene (PE), polypropylene (PP), or a polyester, although said material may alternatively comprise a liquid-permeable material, such as nonwoven material, laminated with a liquid-impermeable material. All materials that are used to produce liquid-impervious outer sheets for absorbent articles can be used. The outer sheet 4 may conveniently be air permeable.

In the illustrated embodiment, the flaps 6, 7 comprise laterally extending parts of the outer sheets 3, 4, although said flaps may alternatively comprise extended parts of solely one of said outer sheets. The flaps may even comprise separate pieces of material fastened to the sides or the underside of the napkin 1.

In the region of the absorbent body 2, the napkin 1 is provided with three adhesive strings 8, 9, 10 on the liquid-impermeable outer sheet 4, these adhesive strings being a central adhesive string 8 that extends along the longitudinal symmetry axis A—A of the napkin throughout the full length thereof, and two shorter adhesive strings 9, 10 that extend on respective sides of the central adhesive string 8, in the front part 5 of the napkin. These adhesive strings 8, 9, 10 are intended for fastening the napkin 1 to the inside of a string panty. Each of the adhesive strings 8, 9, 10 extends in a direction parallel with the longitudinal symmetry axis A—A of the napkin 1.

The sanitary napkin 1 is also provided with two adhesive strings 11, 12 on each flap 6, 7. These adhesive strings 11, 12 are relatively short and extend in directions parallel with the longitudinal symmetry axis A—A of the napkin when the napkin is flat. The adhesive strings 11, 12 on each flap 6, 7 are mutually spaced both longitudinally and laterally, wherewith the foremost string 11 is located furthest from the longitudinal symmetry axis A—A. The length of each adhesive string 11, 12 is suitably shorter than about 30 mm, preferably in the range of 10–20 mm. Each adhesive string will suitably have a width of between 2–15 mm.

Although only two adhesive strings 11, 12 are provided on each flap 6, 7 in the embodiment shown in FIG. 1, it will be understood that the flaps may be provided with more adhesive strings if so desired.

The adhesive in the adhesive strings consists of a pressure-sensitive hotmelt glue, e.g. Ecomelt H145 from Collano, Switzerland. Other commercially available pressure-sensitive adhesives can be used, including adhesives that are pressure-sensitive in a cold state, such as acrylate glue, normally combined with stickiness-enhancing additives, such as polyuterpen, or hotmelt glue, such as styrene and butadiene co-polymers.

In the packaged state of the sanitary napkin, the adhesive strings are covered with a protective layer, e.g. with so-called release paper that consists of a silicone-coated paper and functions to protect the adhesive strings against contaminants, such as dust and the like, and also to prevent the adhesive from drying-out prior to use. The napkin 1 is conveniently provided with a central protective layer that is not removed until the napkin is to be fastened to the inside of a string panty, and also with a protective layer on each flap, this layer being removed prior to folding the flap around the edges of a string panty and fastening the napkin to the outside thereof. These protective layers are not shown in the Figures for the sake of clarity.

The sanitary napkins 1 are manufactured in length production in a continuous production line, by which is meant that the machine direction coincides with the longitudinal axis of the napkin blanks, by placing absorbent bodies on one travelling web of outer sheet material and thereafter placing the other web of outer sheet material to the composite web comprised of the first outer sheet and said absorbent bodies. The adhesive strings and the protective layers may either be mounted subsequent to having delivered an outer sheet and absorbent bodies to the production line, or adhesive strings and protective layers can be mounted on the liquid-impermeable outer sheet prior to combining said sheet with the absorbent bodies and the liquid-permeable outer sheet. Individual sanitary napkins are cut from the resultant web of napkin blanks in the final stage of the manufacturing process.

The adhesive strings can either be applied to the protective layers before said layers are applied to the liquid-impermeable outer sheet, or applied to the liquid-impermeable outer sheet prior to applying said protective layer.

The rear part of the sanitary napkin must be made extremely narrow in order to fit a string panty, whereas the front part of the napkin can be made relatively wide without the napkin protruding beyond the edges of the string panty in whose crotch part the napkin is placed. The major part of the absorption capacity of the absorbent body will therefore, of necessity, lie in the front part of the napkin. Liquid, or fluid, is discharged within a relatively limited area of the napkin, i.e. within the so-called wetting area. Thus, in order to fully utilise the capacity of the absorbent body, it is necessary to be able to transport the liquid discharged by the wearer from the wetting area to the remainder of the absorbent body. This means that the absorbent body must have an effective liquid dispersion capacity. Moreover, the absorbent body for use in a string panty must be thin for reasons of discretion. In order to fulfil these criteria, the absorbent material in the absorbent body 2 is comprised of a layer 13 of dry-formed cellulose fibre material that has been compressed to a density of at least 250 g/dm$^3$, preferably to a density of 300–400 g/dm$^3$, without subsequent defibring and fluffing of the material. Such material is known from WO 94/10956, to which reference is made for further information concerning methods of production and the properties of such material. It is pointed out, however, that such material also has good liquid retention properties. The layer 13 has a weight per unit area of 200–600 g/m$^2$, preferably 250–400 g/m$^2$, meaning that the layer will not have a thickness greater than 1.5 mm. The layer 13 of dry-formed cellulose fibre material may include so-called superabsorbent material, for instance present in a particle form. The superabsorbents may be incorporated in the layer 13 in different ways. For instance, they may be mixed with the fibre material, placed in layers within the layer of fibre material, or disposed therein in some other way. Superabsorbents may be introduced in conjunction with the production of the dry-formed material, although such introduction may take place during other parts of the napkin manufacturing process.

The illustrated embodiment of the absorbent body also includes a layer 14 of material that has good liquid acquisition properties, e.g. a wadding of cellulose fibres, synthetic fibres or mixtures thereof. The presence of such a layer reduces the risk of discharged liquid running on the surface of the napkin and reaching the edge thereof and then staining the panties or some other garment. Although the layer 13 has effective liquid acquisition properties, it may be suitable to provide a separate liquid acquisition layer, and then particularly in the narrow part of the napkin.

The layer 13 of dry-formed cellulose fibres is relatively stiff and it may therefore be expected that the described napkin will be felt to be uncomfortable when worn, owing to the layer 13 possibly chafing and pressing against the inside of the wearer's thighs. Tests have shown, however, that chafing does not occur. One possible explanation of this unexpected comfortableness of the napkin is that the flexural rigidity of the layer 13 causes the layer to be deformed at its tapering part, by bending around a longitudinal axis when the rear part of the string panty, and therewith the narrow part of the absorbent body, is inserted between the thighs of the wearer. The clamping forces exerted by the wearer's thighs will thereby be taken-up by the curvature of the absorbent body. The reaction forces against the wearer's thighs resulting from this curvature of the absorbent body are small, which is possibly why the described sanitary napkin is felt to be comfortable when worn. Such curvature of the absorbent body is also beneficial from an absorption aspect, because the napkin is thereby pressed into tight abutment with the wearer's body within the wetting area. The configuration and dimensions of the described sanitary napkin thus enable the stiffness of the absorbent layer 13 to be used to provide advantages with respect to both function and comfort. When the napkin is worn, the front part of the absorbent body will bend around the labia of the wearer, therewith preventing the edges of the front part of the napkin from chafing the wearer's skin. In order to ensure that the rear edge of the layer 13 will not chafe the wearer's skin, the layer 14 will preferably extend beyond the layer 13 in the rear end-part of the illustrated absorbent body through a distance of 20–30 mm.

It will be understood that the described embodiment can be modified within the scope of the invention. For instance, the absorbent body may include a central outwardly projecting part on that side of the absorbent body that lies proximal to the liquid-permeable outer sheet, so as to increase the contact between absorbent body and labia. Furthermore, the glue pattern on that part of the napkin which includes the absorbent body may be formed differently, for instance the central adhesive string need not extend over the whole of the forward part of the napkin, and the three adhesive strings disposed in the front part of the napkin may be replaced with a single glue string that extends over the major part of the front part of the diaper. That part of the napkin which includes the absorbent body may also be provided with more than three adhesive strings. The adhesive strings within the region of the absorbent body may conceivably be replaced with friction coverings or similar devices. Moreover, adhesive strings may be provided on solely one flap, in which case the flaps must be dimensioned so as to overlap one another when folded-in towards the underside of the string panty after having been folded around the edges thereof. Fastener means other than adhesive may be used to fasten the napkin to a pair of panties, e.g. hook elements of the touch-and-close fastener type, said hooks coacting with panties made from textile-like material. The scope of the invention is therefore limited solely by the contents of the accompanying claims.

What is claimed is:

1. An absorbent article selected from the group consisting of a sanitary napkin, a panty liner and an incontinence protector for women, comprising an absorbent body sandwiched between a liquid-permeable outer sheet and a liquid-impermeable outer sheet, said article having a front part which is intended to face outwards when the article is worn, and a rear part; said absorbent body having a length from 140–260 mm and continuously tapering rearwardly from a section of greatest width at the front part of the article to a rear end part thereof; said absorbent body having a greatest width of 60–80 mm in its front part and a smallest width of 5–20 mm at its rear end, and comprising a layer of dry-formed cellulose fibers that has a density of at least 250 g/dm$^3$; said absorbent body also including an acquisition layer that has liquid acquisition properties and that extends over and beyond the layer of dry-formed cellulose fibers in the rear end part of the absorbent body.

2. The absorbent article according to claim 1, wherein the article includes flexible outwardly projecting flaps which extend outwardly on respective sides of the absorbent body.

3. The absorbent article according to claim 1, wherein the article includes flexible outwardly projecting flaps which extend outwardly on respective sides of the absorbent body.

4. The absorbent article according to claim 1, wherein the layer of dry-formed cellulose fibers has a weight per unit area of 200–600 g/m$^2$.

5. The absorbent article according to claim 4, wherein the article includes flexible outwardly projecting flaps which extend outwardly on respective sides of the absorbent body.

6. The absorbent article according to claim 1, wherein the acquisition layer comprises a fiber wadding of cellulose fibers, synthetic fibers or mixtures thereof.

7. The absorbent article according to claim 6, wherein the article includes flexible outwardly projecting flaps which extend outwardly on respective sides of the absorbent body.

8. The absorbent article according to claim 1, wherein the article includes flexible outwardly projecting flaps which extend outwardly on respective sides of the absorbent body.

9. The absorbent article according to claim 8, wherein the flaps are integral parts of the outer sheets.

10. The absorbent article according to claim 9, wherein at least one fastener means for fastening the article to a pair of panties is provided on that part of the article which includes the absorbent body and at least one other fastening means is also provided on at least one flap.

11. The absorbent article according to claim 10, wherein the fastener means comprise adhesive strings of pressure-sensitive glue.

12. The absorbent article according to claim 11, wherein the fastener means comprise a hotmelt glue.

* * * * *